United States Patent
Nogues et al.

(10) Patent No.: US 11,925,692 B2
(45) Date of Patent: Mar. 12, 2024

(54) NANOPARTICLES PRE-FUNCTIONALIZED USING A SELF-ASSEMBLED MONOLAYER AND METHOD FOR PREPARING SAME

(71) Applicants: Ecole Normale Supérieure Paris-Saclay, Cachan (FR); Centre National de la Recherche Scientifique, Paris (FR)

(72) Inventors: Claude Nogues, Antony (FR); Malcolm Buckle, Antony (FR); Stéphanie Vial, Paris (FR)

(73) Assignees: Ecole Normale Supérieure Paris-Saclay, Cachan (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 17/596,496

(22) PCT Filed: Jun. 12, 2020

(86) PCT No.: PCT/FR2020/051005
§ 371 (c)(1),
(2) Date: Dec. 10, 2021

(87) PCT Pub. No.: WO2020/249912
PCT Pub. Date: Dec. 17, 2020

(65) Prior Publication Data
US 2022/0202953 A1    Jun. 30, 2022

(30) Foreign Application Priority Data
Jun. 12, 2019  (FR) ...................... 1906224

(51) Int. Cl.
*A61K 9/00*    (2006.01)
*A61K 9/50*    (2006.01)
(Continued)

(52) U.S. Cl.
CPC ........ *A61K 47/6923* (2017.08); *A61K 9/5031* (2013.01); *A61K 31/711* (2013.01);
(Continued)

(58) Field of Classification Search
CPC .................................................. A61K 47/6923
See application file for complete search history.

(56) References Cited

U.S. PATENT DOCUMENTS

2011/0165077 A1    7/2011  Qian et al.
2016/0243254 A1    8/2016  Artzi et al.
(Continued)

FOREIGN PATENT DOCUMENTS

CN    106581696 A    4/2017
FR    2863053 B1     4/2007

OTHER PUBLICATIONS

Hurst et al., Self-Assembled Monolayer-Immobilized Gold nanoparticles as Durable, Anti-Stiction Coatings for MEMS, Journal of Microelectromechanical Systems, vol. 20, No. 2, (Apr. 2011), pp. 424-435.
(Continued)

*Primary Examiner* — Paul W Dickinson
(74) *Attorney, Agent, or Firm* — TraskBritt

(57) ABSTRACT

The present invention pertains to the field of pre-functionalized nanoparticles (NPs). It relates more particularly to NPs pre-functionalized using a self-assembled monolayer (SAM) and also to NPs functionalized using biomolecules such that the NPs are stable in solution. These NPs may be used in numerous applications, especially as a diagnostic tool, for depleting a molecule of interest in a solution, and therapeutic tool.

5 Claims, 12 Drawing Sheets

(51) Int. Cl.
    *A61K 31/711*    (2006.01)
    *A61K 47/60*     (2017.01)
    *A61K 47/69*     (2017.01)
    *B82Y 5/00*      (2011.01)
    *B82Y 15/00*     (2011.01)
    *B82Y 40/00*     (2011.01)

(52) U.S. Cl.
    CPC ............... *A61K 47/60* (2017.08); *B82Y 5/00* (2013.01); *B82Y 15/00* (2013.01); *B82Y 40/00* (2013.01)

(56) References Cited

U.S. PATENT DOCUMENTS

2016/0274086 A1    9/2016    Rose-Petruck et al.
2019/0142966 A1    5/2019    Artzi et al.

OTHER PUBLICATIONS

International Search Report for International Application No. PCT/FR2020/051005 dated Sep. 2, 2020, 3 pages.
International Written Opinion for International Application No. PCT/FR2020/051005 dated Sep. 2, 2020, 13 pages.
Li et al., Simple and Rapid Functionlalization of Gold Nanorods with Oligonucleotides using an mPEG-SH/Tween 20-Assisted Approach, Langmuir 2015, vol. 31, No. 28, (Jun. 23, 2015), pp. 7869-7876. https:doi.org/10.1021/acs.langmuir.5b01680.
Wang et al., Role of Thiol-Containing Polyethylene Glycol (thiol-PEG) in the Modification Process of Gold Nanoparticles (AuNps): Stabilizer or Coagulant, Journal of Colloid and Interface Science, vol. 404, (2013), pp. 223-229.

NANOPARTICLES PRE-FUNCTIONALIZED USING A SELF-ASSEMBLED MONOLAYER AND METHOD FOR PREPARING SAME

CROSS-REFERENCE TO RELATED APPLICATIONS

This application is a national phase entry under 35 U.S.C. § 371 of International Patent Application PCT/FR2020/051005, filed Jun. 12, 2020, designating the United States of America and published as International Patent Publication WO 2020/249912 A1 on Dec. 17, 2020, which claims the benefit under Article 8 of the Patent Cooperation Treaty to French Patent Application Serial No. FR1906224, filed Jun. 12, 2019.

TECHNICAL FIELD

The present disclosure relates to the field of pre-functionalized nanoparticles (NP). It relates more particularly to NPs that are pre-functionalized using a self-assembled monolayer (SAM), as well as NPs that are functionalized using biomolecules, such that the NPs are stable in solution. The NPs can be used in a plurality of applications, in particular, as a diagnostic tool, a depletion or concentration tool of a molecule of interest in a solution, and a therapeutic tool.

BACKGROUND

Nanoparticles covered by a layer of SAM are described in the literature. For example, the article by Hurst K. M. et al. (Journal of Microelectromechanical Systems; Volume: 20, Issue: 2, April 2011) describes the immobilization of a SAM made up of p-aminophenyl trimethoxysiiane (APhTS) and 3-mercaptopropyl trimethoxysilane (MPTS) on the NPs in order to stabilize the adhesion of the NPs on the siliconized surfaces of microelectromechanical systems. However, such NPs are not suitable for functionalization using biomolecules.

Other prior art documents describe nanoparticles covered with a thiolated monolayer.

Hurst et al. (2006) describes gold nanoparticles on which DNA molecules are charged, the objective of this study being to charge a maximum of DNA molecules at the surface of the nanoparticles. The authors demonstrate that the maximum charge is achieved when the salinity conditions are brought under control (0.7 M NaCl), and the DNA molecules contain a spacer of the polyethylene glycol (PEG) type.

Wang et al. (RSC Adv. 2017, 7. 3676-3679) describes spherical gold NPs, which are functionalized using a mixed monolayer comprising PEGs and thiolated DNA. The nanoparticles are prepared in 2 steps: functionalization using the thiolated DNA molecules, then using the thiolated PEGs, so as to cover the entire surface of the NP.

Li et al. (Langmuir 2015, DOI: 10.1021/acs.iangmuir.5b01680) describes nanorods (NR) functionalized using molecules of DNA. Since the gold NRs are positively charged, they tend to join together in the presence of negatively charged DNA. The authors propose grating onto the NRs long molecules of PEG and a surfactant, prior to adding thiolated DNA.

The document US 2011/165077 describes the use of gold nanoparticles for imaging. Reporter molecules are grafted onto the surface of the NPs, then these are covered, to saturation point, with a PEG-SH protective layer; this layer prevents the aggregation of the particles, and can be functionalized using specific probes.

The document US 2019/142966 describes the use of metal NPs intended for the treatment of cancer. These NPs are covered with PEG-COOH molecules, in a single step, and then the carboxy groups are functionalized in the presence of SDS with therapeutic molecules and target molecules.

The document US 2016/243254 describes the preparation of nanoprobes as theranostic tools in the treatment of cancer. A first layer of thiolated PEG-COOH is grafted to the surface of the NP; this first layer covers approximately 30% of the surface of the NPs, which represents a maximum coverage rate, on account of the high molecular weight of the PEG-COOHs. A second layer of thiolated DNA-harpin molecules is added, and is sandwiched in between the PEG molecules. In this configuration, the combined presence of a partial coverage rate and the carboxy function is favorable for the appearance of non-specific interactions.

In the field of the NPs intended to be used as a support for fixing biological probes, various constraints must be considered. Firstly, the pre-functionalized or functionalized NPs have to be stable in solution, i.e., they may not aggregate. They must also allow for a specific probes/molecules of interest interaction.

BRIEF SUMMARY

The present disclosure provides a solution to these problems by way of the pre-functionalization of the NPs using a self-assembled monolayer formed of molecules of polyethylene glycol (PEG) having a low molecular weight, the coverage of which is partial. The presence of this pre-layer on the surface of the NPs makes it possible, alone or in combination with other molecules (functionalization), to prepare NPs that are stable in solution. This monolayer is particular in that it is made up of molecules having a low molecular weight (of between 100 and 732 Daltons), the chains of which are short; the bulk in the region of the surface is optimal, which provides the nanoparticles with their innovative properties described in the following.

A representation of the configuration of the elements grafted to the surface of the NPs is shown in FIG. 1.

The functionalization strategy according to the present disclosure is a surface chemistry, which makes it possible to improve the stability of metal nanoparticles, for example, gold, or nanoparticles of the core-shell hybrid type, in buffer and complex media, by controlling the number of ligands (biomolecules) immobilized at the surface of the nanoparticles, by inhibiting the non-specific interactions and optimizing the specific interactions. This technology consists in pre-functionalization prior to immobilization of one or more biomolecules, which act as probes. Either the biomolecules comprise a thiolated group that allows for their direct immobilization on the surface of the NP, or the immobilization of the biomolecules takes place in two steps: 1—immobilization of a linker molecule having on the one hand a thiol (for the immobilization thereof on the metal surface), and on the other hand a reactive functional group (for the immobilization of biomolecules), and then 2—addition of a biomolecule (probe or active molecule) comprising a group that is capable of reacting or interacting with the functional group present on the linker molecule. The method described here is suitable, in particular, for spherical NPs, nanorods, nanocubes, nanotriangles, and nano-urchins.

Moreover, this pre-functionalization allows for an optimization of the density of the probes, a homogeneous distribution of the probes, and an absence of non-specific interactions. In particular, the present disclosure makes it possible to have NPs that are functionalized using probes and the density of which is low and optimized in order to achieve a high degree of sensitivity of detection. It is also possible to combine a plurality of different probes while preserving a controlled density and distribution for each of the probes.

DETAILED DESCRIPTION

Figure 1:
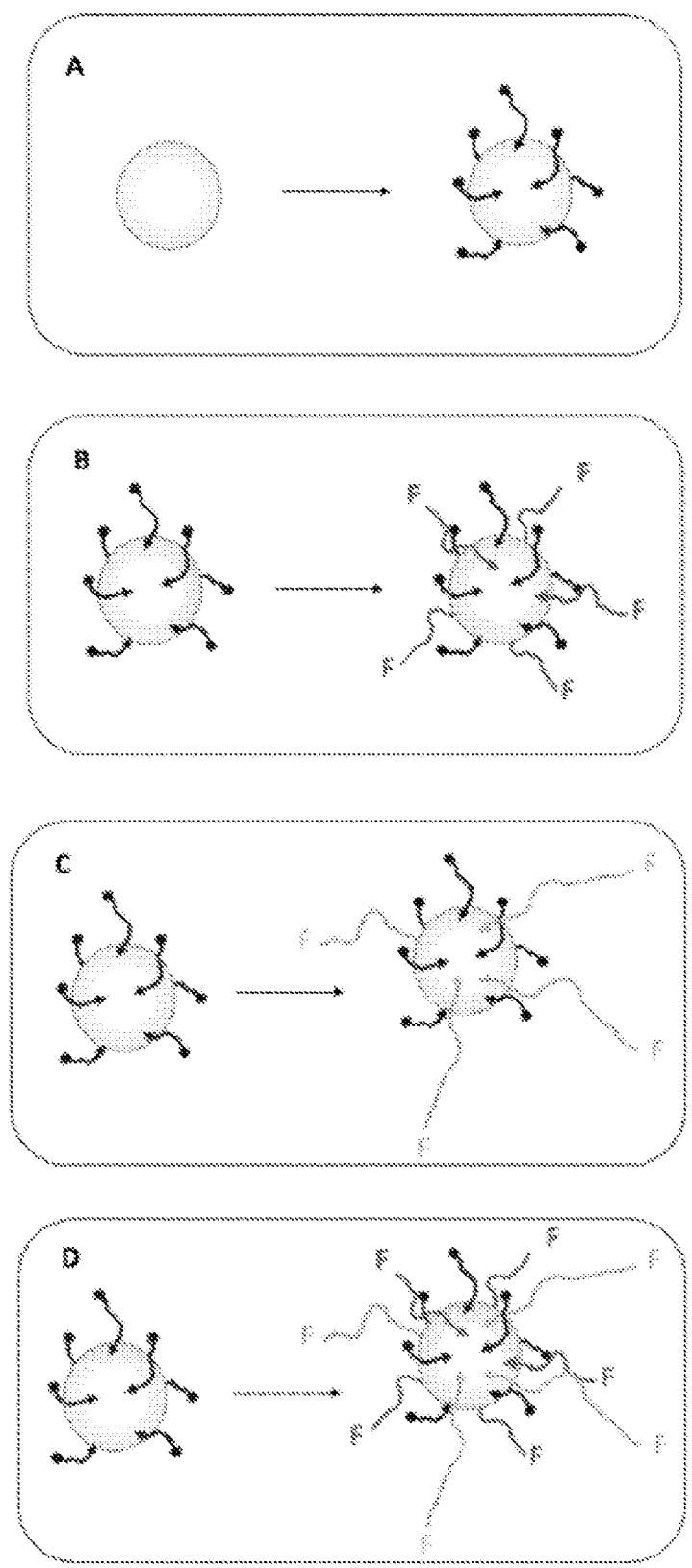
FIG. 1: View of the technology for the functionalization of NPs. A) pre-functionalization using a SAM made up of molecules M (represented by a short black curve); B) M+L-PEG (represented by a long light gray curve); C) M+PEG-F or biomolecule (represented by a medium gray curve of intermediate length); D) M+PEG-F or biomolecule+L-PEG. F represents a functional group.

A first object of the present disclosure relates to a nanoparticle comprising a metal surface that is pre-functionalized using a self-assembled monolayer (SAM) formed by a matrix of molecules bearing a thiol function at one of the ends, the other end being inert, the nanoparticle being characterized in that the coverage rate W of the monolayer is between 1.5% and 99%.

The particularity of the self-assembled monolayer is that it is applied to the surface of the NPs before their functionalization, and that it is unsaturated. It plays a role in protecting the surface. This monolayer is formed of molecules M of formula (I):

in which:
n represents the number of $CH_2$, where $3 \leq n \leq 11$
m represents the number of ethylene glycol, where $1 \leq m \leq 12$.

The molecular weight of the molecule M is between 100 and 732 Daltons.

Overall, a coverage rate W of a minimum of 1.5% is necessary in order to observe the effects of the SAM layer; a low coverage rate allows for a high density of biomolecules at the surface of the NP, which may be of interest, for example, when 2 different biomolecules are present. In contrast, the coverage rate W may be high, close to saturation point (99%, for example), allowing for deposition of a single molecule; the only limit of this approach may be that of detection, due to the absence of an appropriately sensitive tool. In any case, the fact of pre-functionalizing the surface of the NP makes it possible to immobilize the biomolecules in a controlled manner, i.e., to ensure that the average distance between the immobilized biomolecules is homogeneous.

In particular embodiments, the coverage rate W may be between 3% and 80%, for example, between 10% and 50%, or between 5% and 30% depending on the applications, in particular, 2%, 5%, 10%, 20%, 30%, 40%, 50%, 60%, 70%, 80%, 90%, 95%, 98%.

Within the meaning of the present disclosure, "coverage rate" means a theoretical initial coverage rate; this corresponds to the surface of the molecule, and is calculated according to the following formula (2):

(imprint expressed in $nm^2$)×100/surface area of the nanoparticle

Within the meaning of the present disclosure, a "nanoparticle" (NP) may be a spherical nanoparticle (NS), a nanorod (NR), a cubic nanoparticle (NC), or a nanotriangle (NT), or a nano-urchin. These may, in particular, be spherical gold nanoparticles, the diameter of which is between 10 and 80 nm, nanorods of which the aspect ratio is between 2.5 and 5, and nanocubes having an edge of 40 nm, or nanotriangles of which the edges are between 30 and 100 nm and 10-40 nm thick. The NPs can also be hybrid NPs of the same shape (spheres, nanorods, etc.) comprising, for example, a core of the oxide type (e.g., iron oxide, silicon oxide) or metal and a metal shell (e.g., gold). The metal surface of the core-shell hybrid nanoparticles is similar to the surface of the metal nanoparticles, and the method for calculating the surface thereof is identical.

The surface area of the molecule depends on its shape, and this must be known in order to determine the coverage rate.

In the case of a spherical nanoparticle, the surface area corresponds to the following formula (3):

$4\pi r^2$ where r corresponds to the radius of the nanoparticle.

In the case of a nanorod, the surface area corresponds to the following formula (4):

$2\pi rl + 2\pi r^2$ where r corresponds to the radius of the nanorod, and l corresponds to the length thereof.

In the case of a nanocube, the surface area corresponds to the following formula (5):

$6a^2$ where a corresponds to an edge of the nanocube.

In the case of a nanotriangle, the surface area corresponds to the following formula (6):

(ph/2)+b where p corresponds to the perimeter of the base, h to the height of the slope, and b to the area of the base.

The molecules present on the surface of the NPs for their pre-functionalization or their functionalization may be selected from the following molecules: molecules M as defined above, molecules L-PEG and PEG-F as defined in the following, and double stranded DNA (dsDNA) or single stranded DNA (ssDNA), RNA, proteins such as antibodies or peptides, aptamers, etc.

Thus, in order to determine the coverage rate it is also necessary to know the theoretical imprints of the molecules present at the surface of the NPs:

imprint of M and PEG-F=0.23 $nm^2$ [1]
L-PEG imprint=0.45 $nm^2$ [2]
dsDNA imprint=3.14 $nm^2$ In an advantageous embodiment, the pre-functionalized nanoparticles according to the present disclosure are functionalized using at least one L-PEG molecule, the coverage rate X of which is at least 1%, preferably between 1% and 10%.

"L-PEG molecule" means a molecule of thiolated polyethylene glycol of long height and having a high molecular weight.

The L-PEG molecules may be of formula (7):

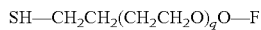

in which:
q represents the number of ethylene glycol, where $20 \leq q \leq 500$;
F represents a functional group such as $CH_3$, OH, COOH, $NH_2$, etc.

The molecular weight of the L-PEG molecule is greater than or equal to 800 Daltons.

The functionalization using L-PEG molecules is of particular interest for stabilizing the NPs in a PBS solution. It may be combined with pre-functionalization using molecules M in order to prepare "ready-to-use" NPs on which one or more biomolecules can be adsorbed.

Moreover, when the group F is different from $CH_3$ or OH, it may interact and/or react with biomolecules, in order to add probes on the surface of the NPs.

In a particular embodiment of the present disclosure, the pre-functionalized nanoparticles according to the present disclosure are functionalized using at least one thiolated molecule, the thiolated molecule being:
either a thiolated linker molecule comprising a thiol function at one of the ends and bearing at the other end thereof an active or reactive group that is capable of interacting with a biomolecule;
or a biomolecule comprising a thiol function.

The nanoparticles can furthermore be functionalized using an L-PEG molecule as described above.

In an embodiment of interest, the thiolated linker molecule is a PEG-F molecule, in which F is an activatable functional group such as a COOH, and the coverage rate Y of which is at least 1%. The overall coverage rate of the surface of the NP may be partial or total (saturation), depending on the applications. In a preferred embodiment, the overall coverage is partial.

"PEG-F" means a molecule of thiolated polyethylene glycol.

The PEG-F molecules may, for example, be of formula (8):

HS(CH$_2$)$_r$(OCH$_2$CH$_2$)$_p$O—F, in which:

r represents the number of CH$_2$ and is a whole number greater than or equal to 3;

p represents the number of ethylene glycol, where 2≤p≤12, and

F represents a functional group such as CH$_3$, COOH, NH$_2$, etc.

The molecular weight of the PEG-F molecule may be low or high, extending as far as over 800 kDa.

In an alternative embodiment, the linker molecules may be L-PEG molecules comprising an activatable functional group.

In another embodiment of interest, the pre-functionalized nanoparticles according to the present disclosure are functionalized using a thiolated biomolecule, which serves as a probe (referred to as "thiolated probes"), such as nucleic acids (DNA, RNA, PNA, etc.), proteins (antibodies, antigens, hormones, etc.), peptides, hormones, sugars, fatty acids, or indeed entire cells.

In another embodiment of interest, the thiolated biomolecules are small molecules, such as drugs, sandwiching or complexing, referred to here as "active molecules." These active molecules may also be bound by way of an activatable functional group present on the PEG-F or L-PEG molecules.

When the thiolated molecule is a double stranded or single stranded DNA, the coverage rate Z is at least 10%. The overall coverage rate of the surface of the NP may be partial or total (saturation), depending on the applications. In a preferred embodiment, the overall coverage is partial.

In a preferred embodiment, when the PEG-F is short, L-PEG molecules are added at the rate of 1% in order to stabilize the NPs.

Within the meaning of the present disclosure, "thiolated probe" means a biomolecule, which plays the role of a probe that is capable of specifically interacting with (capturing) a molecule of interest located in an aqueous medium (buffer solution, for example) or complex medium (culture medium, biological medium, body fluids, liquid matrix such as blood, plasma, serum, urine, tears, cellular extracts, etc.). The biomolecules functioning as probes are fixed to the support of the NP (i) either by direct interaction of a thiolated group present on the biomolecules with the surface of the NP, (ii) or by way of a thiolated molecule at one of the ends thereof and bearing, at the other end, an active or reactive group, which is capable of reacting with (binding with) the binding molecule by formation of a "strong" bond (for example, a covalent bond such as an amide bond, chelation, a strong affinity of the "tag" type such as the streptavidin-biotin bond); the thiolated molecule is referred to here as a "linker molecule."

Once the substrate is protected by the protective layer SAM as described above, an additional step of deposition of thiolated probes follows, immediately or just before use, after a few hours, days, or months.

These thiolated probes may be:

directly thiolated probes, requiring an incubation time, which depends on the concentration, which is generally low (of the micromolar order, or having a lower concentration);

thiolated molecules having a reactive amine or carboxyl group, a double or triple carbon-carbon, epoxy, click chemistry, etc., bond, thiolated molecules having an active group that interacts with complementary molecules in order to form a sandwich, for example, biotin-streptavidin-biotin, etc.

A second object of the present disclosure relates to a method for preparing a nanoparticle comprising a metal surface that is pre-functionalized using a self-assembled monolayer (SAM) formed by a solution of molecules bearing a thiol function at one of the ends, the other end being inert, the method comprising the following steps:

adding molecules M that are capable of forming a self-assembled monolayer, so as to achieve a coverage rate W of between 1.5% and 99%, stirring for a time period of at least 5 minutes.

A method of this kind makes it possible to prepare pre-functionalized NPs, which are stable in water and in the PBS. The NPs thus prepared may be stored for several months, at 4° C., until use.

It is possible to add a surfactant during this method. The surfactant used may be selected from all the surfactants known to a person skilled in the art, in particular, SDS, CHARS, NP40, TWEEN® 20 (SDS: sodium dodecyl sulfate, CHARS: 3-[(3-cholamidopropyl)dimethylammonio]-1-propanesulfonate), etc. A person skilled in the art is familiar with the use of surfactants for preparation of NP in solution.

In a particular embodiment of the present disclosure, furthermore a solution of L-PEG molecules is added to the solution of NPs pre-functionalized using the SAM layer, in order to achieve a coverage rate Y of between 1 and 10%, and then incubation is carried out, while stirring, for a minimum time period of 5 minutes, generally between 5 minutes and 1 hour.

The NPs that are pre-functionalized using molecules M, and optionally functionalized using L-PEG molecules, can furthermore be functionalized using thiolated molecules and/or biomolecules. In an alternative embodiment, the L-PEG molecules may be added after the PEG-F molecules.

A preparation method of this kind comprises the following steps:

adding a thiolated molecule selected from a thiolated linker molecule capable of interacting with a biomolecule or a thiolated biomolecule, stirring, for example, for a time period of between 5 minutes and 24 hours, if the thiolated molecule is a biomolecule, placing it into buffer conditions suitable therefor, removing the excess thiolated molecule, for example, by means of centrifugation, redispersing in a suitable solution (distilled water, buffer solution comprising a surfactant, etc.), if the thiolated molecule is an activatable molecule, adding the activator (ECD/NHS or PDEA, for example), incubating for at least 5 minutes, centrifuging, and redispersing in a buffer solution prior to incubating with a known solution of biomolecules to be immobilized, if the thiolated molecule is a thiolated linker molecule, subsequently optionally adding a solution of biomolecules capable of interacting with the group of the linker molecule.

This method makes it possible to prepare different types of functionalized NPs, depending on the steps carried out:

NP pre-functionalized M

NP pre-functionalized M+L-PEG

NP pre-functionalized M+PEG-F

NP pre-functionalized M+L-PEG+PEG-F

NP pre-functionalized M+thiolated biomolecule (e.g., DNA)

NP pre-functionalized M+L-PEG+thiolated biomolecule, and so on, with every type of biomolecule suitable for use as a probe.

Embodiments are set out in FIG. 1.

The advantage of the method that starts with the preparation of pre-functionalized NPs with the molecule M at different coverage rates is that the NPs are stable for the following functionalization steps, which can be carried out in water and also in buffer solutions. The molecules M are small, short molecules, of low molecular weight, and inert. The pre-functionalization using the molecule M ensures that the functionalization is homogeneous over the whole surface of the NPs, whatever their size and their shape. Moreover, it ensures that the immobilized biomolecules are not denatured, and are oriented toward the solution and not toward the surface of the NP. In addition, the molecule M prevents the non-specific interactions.

A third object of the present disclosure relates to the use of the nanoparticles according to the present disclosure.

The functionalized NPs may be used in numerous applications that are well known to a person skilled in the art in the medical, agri-food, and environmental field.

They can, in particular, be used to detect molecules of interest in solution, typically in diagnostic tests.

The present disclosure thus relates to a method for detecting a molecule of interest in a solution, in particular, a complex medium, comprising the steps of:
  bringing a solution into contact with at least one functionalized nanoparticle as defined above,
  detection by SPR, strip test, or any other suitable method, of a specific signal when a biomolecule interacts with one of the components of the solution.

The functionalized NPs according to the present disclosure can also be used for depleting particular molecules, whether these be molecules of interest that are intended to be recovered, or indeed undesirable molecules, which are intended to be eliminated.

The present disclosure thus relates to a method for detecting molecules of interest present in a solution, in particular, a complex medium, the method comprising the steps of:
  a) bringing a solution containing the molecule of interest into contact with a functionalized nanoparticle as defined above,
  b) incubating the solution in the presence of the nanoparticles,
  c) recovery of the nanoparticles,
  d) optionally, repeating steps a) to c) until the solution of molecule of interest has been exhausted.

Using functionalized NPs in order to allow for their targeting at target cells and/or the grafting of therapeutic compounds has long been envisaged in the treatment of cancers. In radiotherapy, the NPs, which can be activated by means of X-rays may constitute a major advancement in the practice of radiotherapy intended for destroying tumors under control. The NPs can also be used in approaches of photothermal therapy, one of the most promising applications of gold nanoparticles for combatting cancer. The concept is that of injecting gold nanoparticles into the blood circulation of patients. On account of their structure, the nanoparticles tend to become fixed in the cancerous tissues, but it is possible to direct them even more specifically toward the tumor, by covering them with particular molecules (functionalization). They are then "heated" using a laser light. The heat given off by the NPs creates irreversible lesions in the cancerous cells. This technique is currently being tested in a plurality of clinical trials in cancers of the head or neck, or indeed of the lungs and prostate.

Thus, the present disclosure relates to the use of a functionalized NP according to the present disclosure in the treatment of cancer, in particular, by radiotherapy or photothermal therapy. The controlled photothermal therapy could allow for salting out of a therapeutic molecule previously grafted onto the nanoparticle, without affecting the cell or the target organ.

The present disclosure relates to the use of a functionalized NP according to the present disclosure for medical imaging.

The solution into which the NPs are added may be vary varied in nature. It may be simple media (water, PBS, model media), or complex media (body fluids, waste water, effluent, etc.). It may also, more generally, be a matrix in which, or upon contact with which, the NPs can be dispersed. This matrix may be a gel, sand, or any flat surface likely to comprise molecules of interest on the surface thereof.

In a particular embodiment, the solution is a complex biological medium such as a cellular extract, a bacterial culture extract, a biological human sample selected from serum, blood, urine, amniotic fluid, tears, etc., an aquatic medium selected from waste water, polluted water, or water likely to be such, seawater, water from an aquarium, etc.

EXAMPLES

Terms

Thiolated molecule: "thiolated linker molecule capable of interacting with a biomolecule" or "thiolated biomolecule"

W is the coverage rate of the pre-layer formed of molecules M.

X is the L-PEG coverage rate

Y is the PEG-F coverage rate

Z is the thiolated DNA coverage rate

Example 1

General Protocol for
Pre-Functionalization/Functionalization of
Nanoparticles

Before any pre-functionalization, it is preferable to remove the excess surfactant (citrate, for example) in the solutions of nanoparticles (NP) (diluted in water). In order to achieve this, in advance the NP solutions are centrifuged, the supernatant is removed, and the NP cake is redispersed in the same volume of distilled water. The centrifugation speed and time are to be adjusted depending on the size of the NPs.

Example of the Preparation of Functionalized Spherical NPs

Proceeding from an NP solution (size extending from 10 to 80 nm diameter), the following steps are carried out:
  a) adding molecules M so as to achieve a coverage rate W of between 1.5% and 99%,
  b) stirring for a time period of between 5 minutes and 4 hours,
  c) optionally adding L-PEG molecules so as to achieve a coverage rate Y of between 1% and 10%,
  d) stirring for a time period of between 5 and 60 minutes,
  e) adding a thiolated molecule (either a thiolated molecule capable of interacting with a biomolecule, or a thiolated biomolecule) in order to achieve a coverage rate Y of at least 1% or Z=at least 10%), f) stirring for a time period of between 5 minutes and 24 hours,
g) if the thiolated molecule is a biomolecule, placing it into buffer conditions suitable therefor,
h) centrifugation in order to remove the excess thiolated molecule,
i) Redispersing in a suitable solution (distilled water, buffer solution comprising a surfactant, etc.).

Example 2

The Pre-Functionalization of the Surface of the Gold Nanoparticles Using Molecules M Improves the Stability of the Nanoparticles in a Solution of PBS a) Case of Spherical Nanoparticles A solution of molecules M (W=24%) is added to a solution of nanoparticles. The mixture is stirred for several hours (at least 4 hours), then 0 and 0.005% surfactant, a phosphate buffer solution of pH 7.4, and NaCl, is added. The NPs are then dispersed in PBS (phosphate 10 nM, pH=7.4, and 0.1 M NaCl) in the presence or absence of 0.005% surfactant.

Figure 2:
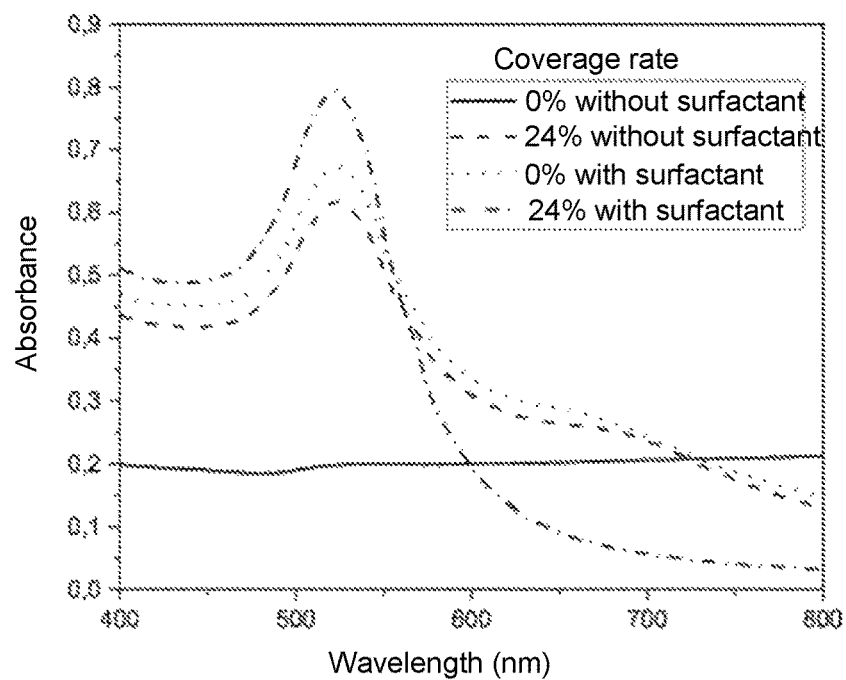
FIG. 2: Absorbance spectrum of NS pre-functionalized with molecules M depending on the coverage rate, in PBS in the presence or absence of a surfactant. Spherical nanoparticles of 20 nm; stirring time=4 hours, M (n=11, m–4).

The data relating to the stability of the nanoparticles are set out in FIG. 2.

It is observed that, without molecules M, the nanoparticles are not stable, and aggregate. In contrast, the presence of molecules M allows for the nanoparticles to be kept in suspension. According to the absorbance spectra of FIG. 2, an improvement in the stability of the nanoparticles in the PBS in the presence of a surfactant is observed, since the plasmon band is refined.

b) Case of Nanorods

A solution of molecules M, and then 0.005% surfactant, is added to a solution of nanorods (NR). The mixture is stirred for 30 minutes, and then a phosphate buffer solution of pH 7.4, and NaCl, is added. The NPs are then dispersed in PBS (phosphate 10 nM, pH=7.4, and 0.1 M NaCl) in the presence of 0.005% surfactant.

Figure 3:
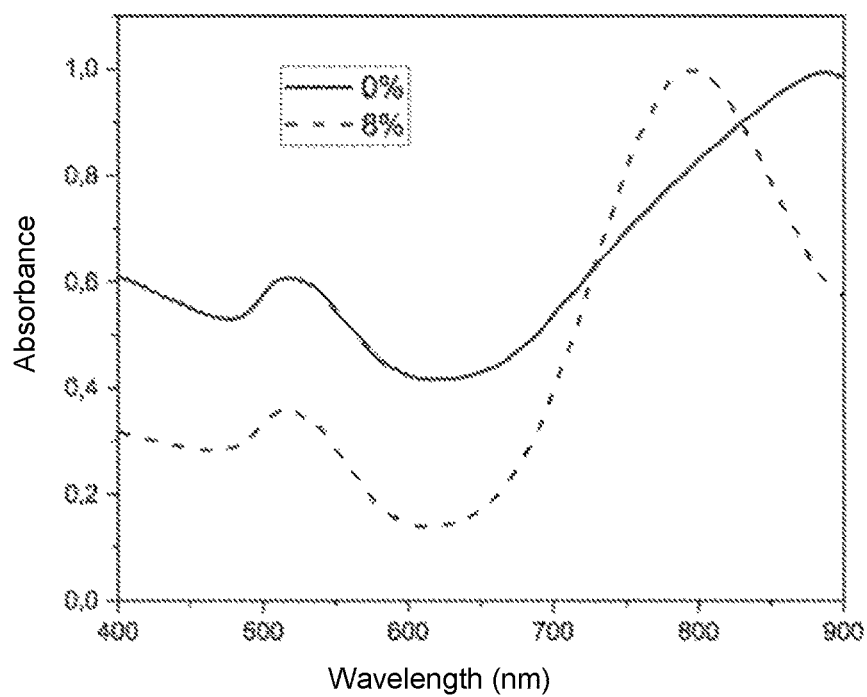
FIG. 3: Absorbance spectrum of NR pre-functionalized with molecules M depending on the coverage rate, in PBS in the presence of a surfactant. Nanorods λ=800 nm; stirring time=30 minutes, M (n=11, m=4), W=8%.

The data relating to the stability of the nanoparticles are set out in FIG. 3. It is observed that, without molecules M, the nanoparticles are not stable, and aggregate. In contrast, the presence of molecules M allows for the nanoparticles to be kept in suspension in PBS+0.005% surfactant.

The rest of the experiments were carried out using spherical NPs.

Example 3

The Nanoparticles Pre-Functionalized Using Molecules M can be Rinsed and Redispersed in a Solution of PBS in the Presence of Surfactant A solution of molecules M is added to a solution of nanoparticles. The mixture is stirred for 5 minutes or 4 hours, centrifuged, and redispersed in a solution of PBS 1× in the presence of 0.005% surfactant.

"PBS 1×" means a solution comprising 137 mM NaCl, 10 mM phosphate, 2.7 mM KCl, and having a pH of 7.4.

Various protocols were tested:
a) Spherical nanoparticles of 20 nm, incubated for 5 minutes in a solution of molecules M.

Figure 4:
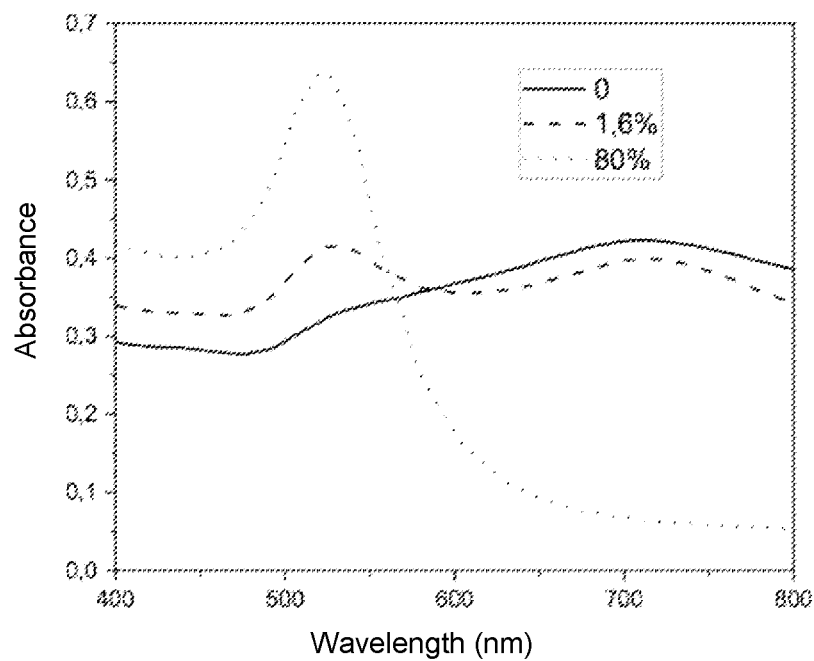
FIG. 4: Absorbance spectrum of NS pre-functionalized with molecules M depending on the coverage rate, in PBS after centrifugation. Nanoparticles of 20 nm; coverage rate between 1.6 and 80%; stirring time=5 minutes, M (n=11, m=4), PBS+0.005% surfactant.

The data relating to the stability of the nanoparticles are set out in FIG. 4.
b) Spherical nanoparticles of 20 nm, incubated for 4 hours in a solution of molecules M.

Figure 5:
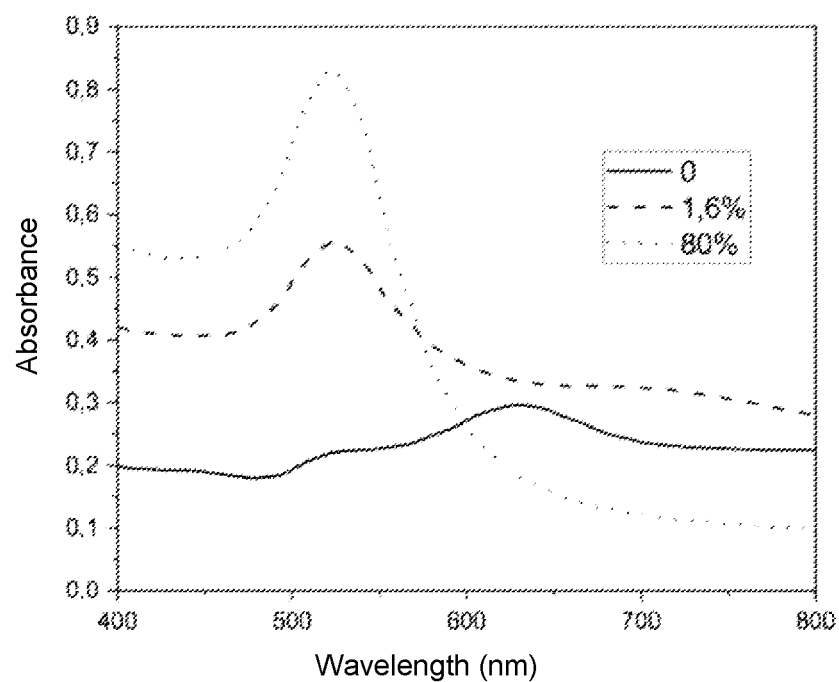
FIG. 5: Absorbance spectrum of NS pre-functionalized with molecules M depending on the coverage rate, in PBS in the presence of a surfactant. Nanoparticles of 20 nm; coverage rate between 1.6 and 80%; stirring time=4 hours, M (n=11, m=4), PBS+0.005% surfactant.

The data relating to the stability of the nanoparticles are set out in FIG. 5.
c) Spherical nanoparticles of 40 nm, incubated for 4 hours in a solution of molecules M.

Figure 6:
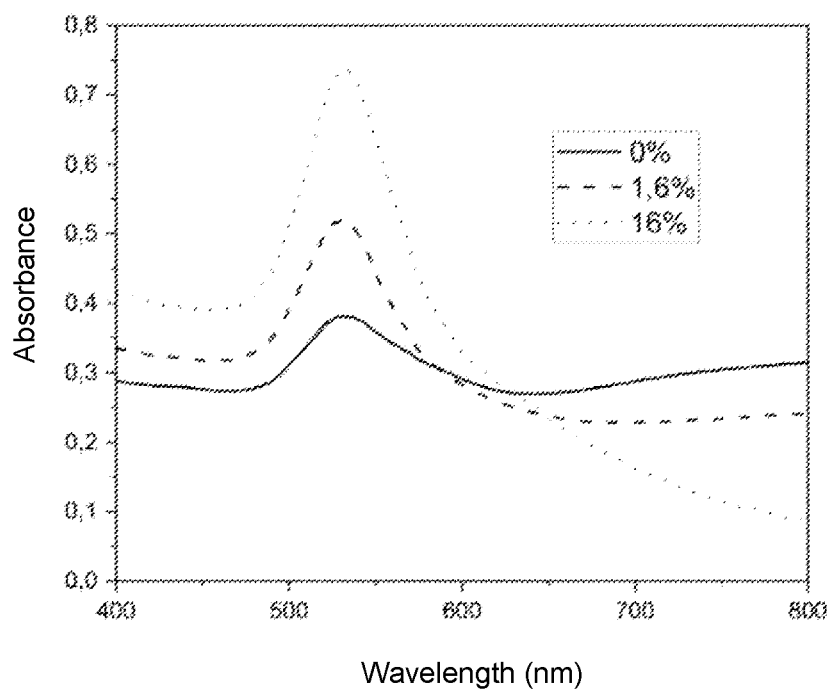
FIG. 6: Absorbance spectrum of NS pre-functionalized with molecules M depending on the coverage rate, in PBS in the presence of a surfactant. Commercial nanoparticles of 40 nm (ref: 741981 Sigma Aldrich); coverage rate 0, 1.6 and 16%; stirring time=4 hours, M (n=11, m=12), PBS+0.005% surfactant.

The data relating to the stability of the nanoparticles are set out in FIG. 6.

These results clearly show that the stability of the nanoparticles increases with the coverage rate of the solution of molecules M.

Example 4

The Functionalization Using an L-PEG Molecule Improves the Stability of the Nanoparticles Pre-Functionalized Using Molecules M in a PBS Solution a) Pre-Functionalization Alone For the pre-functionalization alone, a solution of molecules M for W=1.6 to 80% was added to a solution of nanoparticles. The mixture was stirred for several minutes or hours (5 minutes to 24 hours), centrifuged, and redispersed in an appropriate solution.

b) Pre-Functionalization Followed by Functionalization Using L-PEG Molecules

For the pre-functionalization followed by functionalization using L-PEG molecules, a solution of molecules M, in order to achieve a coverage rate W=5%, is added to a solution of nanoparticles. Following at least 5 minutes of stirring, an L-PEG solution is added for a coverage rate of 0, 1 and 10%. The mixture is stirred again for 15 minutes, then centrifuged, and redispersed in a solution of PBS (1×).

Figure 7:
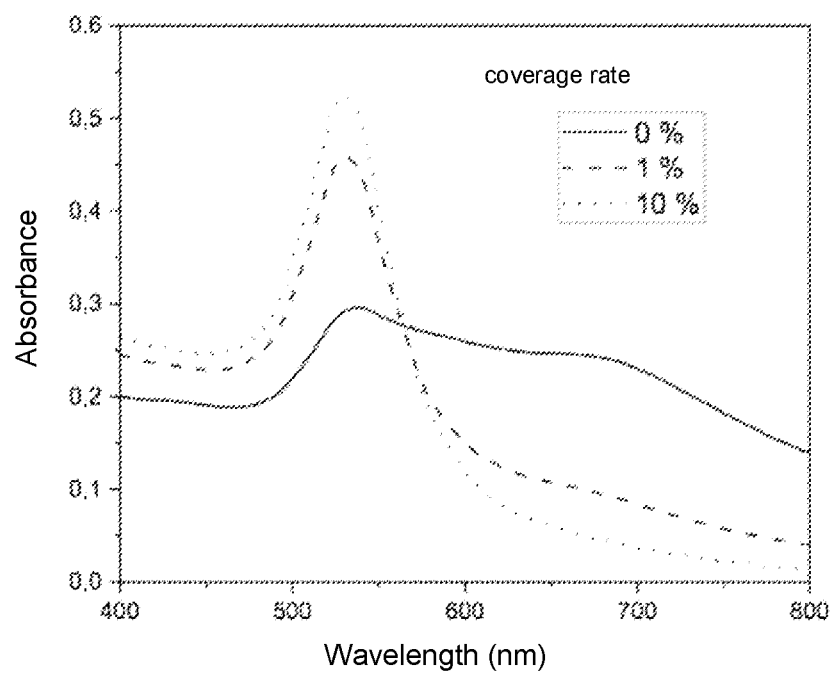
FIG. 7: Absorbance spectrum of NS pre-functionalized with molecules M, and NP pre-functionalized with molecules M and functionalized with the L-PEG (W=5%) dispersed in PBS with different L-PEG coverage rates (X=0, 1, 10%). Nanoparticle of 40 nm (ref: 741981 Sigma Aldrich), incubation time L-PEG=5 minutes, M (n=11, m=4), L-PEG molecular weight=6000, F=$CH_3$.

The data relating to the stability of the nanoparticles are set out in FIG. 7.

These results show that the addition of L-PEG, from X=1%, makes it possible to stabilize the NPs covered by a monolayer of molecules M in PBS, for a low coverage rate, in this case W=5%. Indeed, the plasmon band is refined with L-PEG, confirming the improvement in the stability.

Example 5

The Pre-Functionalization of Nanoparticles Using Molecules M Improves the Stability of the Nanoparticles Functionalized Using a Thiolated Molecule in a Solution of PBS a) Functionalization Using Thiolated Carboxyl Molecules, without Pre-Functionalization.

A solution of PEG-COOH was added to a solution of nanoparticles, such that the coverage rate Y was 1.6%. The mixture was stirred for 30 minutes, centrifuged, and redispersed either in H2O or in PBS 1×+0.005% surfactant.

b) Pre-Functionalization Followed by Functionalization Using Thiolated Carboxyl Molecules A solution of molecules M was added to a solution of nanoparticles, such that the theoretical initial coverage rate Y was between 1.6% and 80%. Following 5 minutes of stirring, a solution of PEG-COOH was then added in order to achieve a coverage rate Y of 1.6%. The mixture was stirred for 30 minutes, centrifuged, and redispersed either in distilled water or in PBS 1×+0.005% surfactant.

Figure 8:
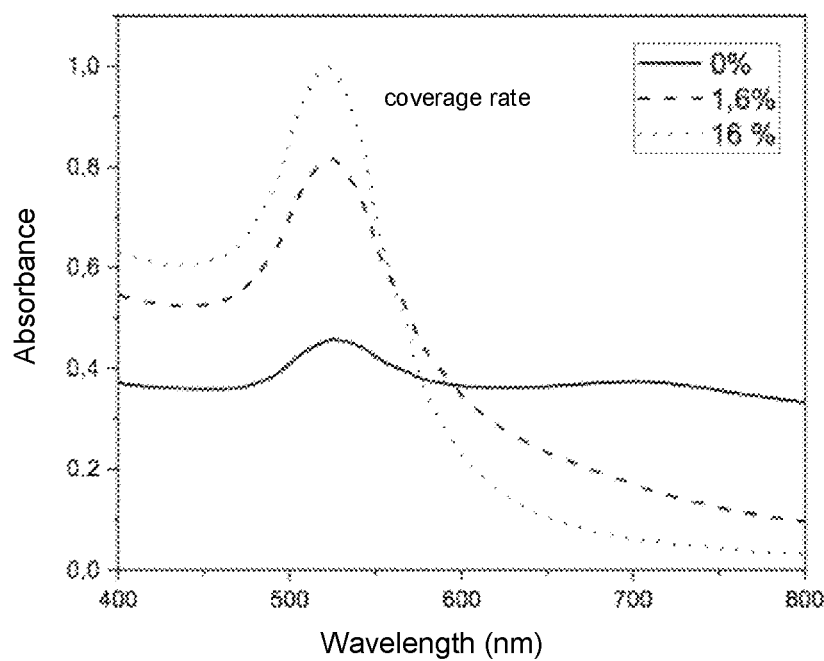
FIG. 8: Absorbance spectrum of NS functionalized with thiolated molecules bearing a COOH function (Y=1.6%) dispersed in PBS with different coverage rates of molecules M (W=0, 1.6 and 16%). Nanoparticles of 20 nm. M (n=11, m=4) and PEG-COOH (r=11, p=6).

The data relating to the stability of the nanoparticles are set out in FIG. 8.

These results show that the NPs functionalized with PEG-COOH alone aggregate in the PBS. The fact of pre-functionalizing the NPs using a solution of molecules M makes it possible to improve the stability of the NPs in solution, specifically from a coverage rate W=1.6%. The stability is improved further by increasing the incubation time and W, i.e., by increasing the density of molecules M at the surface of the NPs (in this case W=16% on the curve reflecting the highest stability).

Example 6

The Functionalization Using L-PEG Molecules Improves the Stability of the NPs Pre-Functionalized Using Molecules M and Functionalized Using a Thiolated Molecule in a PBS Solution A solution of molecules M was added to a solution of NP, so as to achieve a coverage rate W=5%. A solution of L-PEG was then added, such that the coverage rate X was 0 or 10%. A solution of PEG-COOH was then added in order to achieve a coverage rate Y=5%. The mixture was stirred, centrifuged, and redispersed either in distilled water or in PBS 1×+0.005% surfactant.

Figure 9:
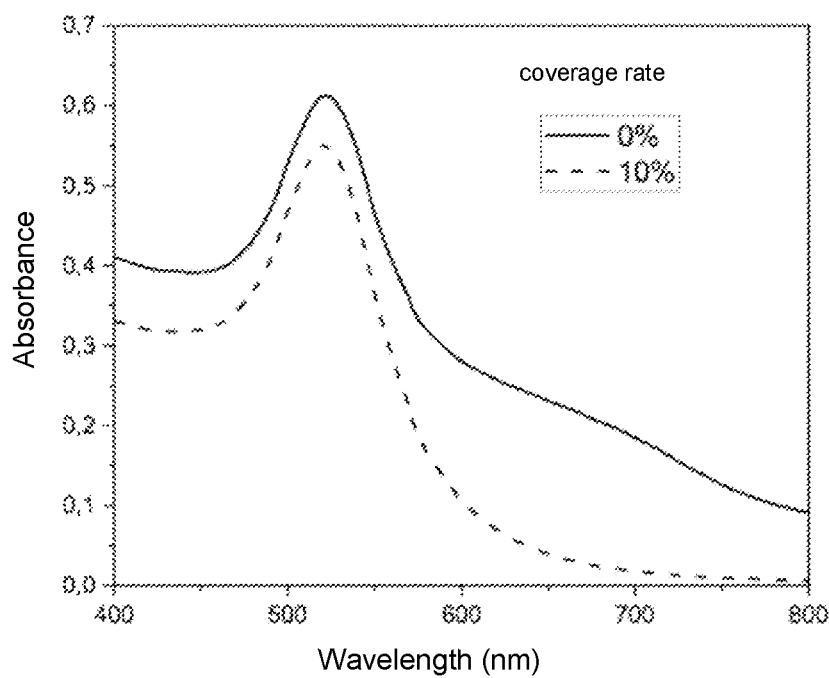
FIG. 9: Absorbance spectrum of NS pre-functionalized with molecules M and functionalized PEG-COOH (W=5%, Y=5%) depending on the presence of an L-PEG functionalization, dispersed in PBS having different L-PEG coverage rates (X=0 or 10%); NS size=20 nm. M (n=11, m=4), L-PEG molecular weight=6000 and F=$CH_3$, PEG-COOH (r=11, p=6).
Figure 10:
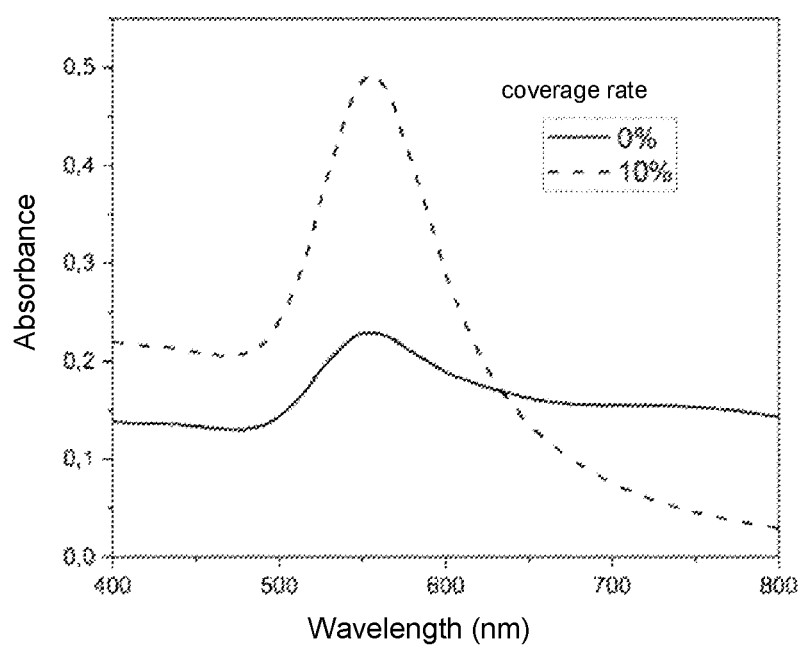
FIG. 10: Absorbance spectrum of NS pre-functionalized with molecules M and functionalized PEG-COOH (W=5%, Y=5%) dispersed in PBS having different L-PEG coverage rates (X=0 or 10%); NS size=80 nm commercial (ref 742023 Sigma Aldrich). M (n=11, m=4), L-PEG molecular weight=6000, F=$CH_3$, PEG-COOH (r=11, p=6).

The data relating to the stability of the nanoparticles are set out in FIG. 9 for spherical NPs of 20 nm, and in FIG. 10 for spherical NPs of 80 nm.

It is noted that adding 10% L-PEG increases the stability of the NPs that are pre-functionalized and functionalized using a thiolated molecule (in this case PEG-COOH), in particular, at low coverage rates of molecules M and of thiolated molecules (5% coverage each).

Example 7

The Pre-Functionalization Using Molecules M Improves the Stability of the NPs Functionalized Using a Thiolated Molecule in a PBS Solution: Case of a Thiolated DNA Molecule a) Functionalization Using Thiolated DNA Molecules, without Pre-Functionalization A solution of DNA was added to a solution of nanoparticles, in order to achieve a coverage rate Z of at least 12.5%. The mixture was stirred for 1 hour, then 0.005% surfactant, and phosphate buffer, and NaCl, was added. The mixture was stirred for 18 hours, centrifuged, and redispersed in PBS 1×.

b) Pre-Functionalization Followed by Functionalization Using Thiolated DNA Molecules A solution of molecules M was added to a solution of NP, so as to achieve a coverage rate 1.6 and 80%. A solution of DNA was then added, in order to achieve a coverage rate Z of at least 12.5%. Following 1 hour of stirring, 0.005% surfactant, phosphate buffer, and NaCl, was added. The mixture was stirred for 18 hours, centrifuged, and redispersed in PBS 1×.

Figure 11:
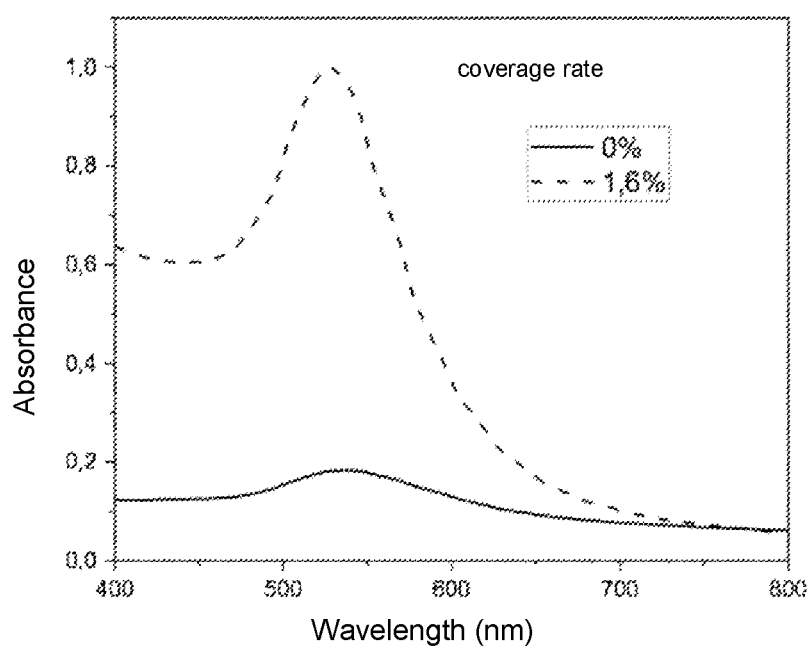
FIG. 11: Absorbance spectrum of NS pre-functionalized with molecules M and functionalized DNA (W=0 or 1.6%; Z=12.5%) dispersed in PBS; M (n=11, m=4); NS size=20 nm.

The data relating to the stability of the nanoparticles are set out in FIG. 11.

It is noted that the NPs functionalized with DNA aggregate in the PBS. However, pre-functionalization using molecules M improves the stability proceeding from a coverage rate W of 1.5%. The stability can be improved further by increasing the incubation time and W, i.e., by increasing the density of molecules M at the surface of the NPs (data not shown).

Example 8

The L-PEG Functionalization Improves the Stability of the NPs Pre-Functionalized Using Molecules M and Functionalized Using a Thiolated DNA in a PBS Solution A solution of molecules M was added to a solution of nanoparticles, so as to achieve a coverage rate W of 1.6 and 80%. A solution of L-PEG was then added in order to achieve a coverage rate X of between 1 and 10% following 30 minutes of incubation. The mixture was stirred for 15 minutes. A solution of SH-DNA was then added, in order to achieve a theoretical initial coverage rate of at least 12.5%. Following addition of the DNA solution, 0.005% surfactant, phosphate buffer of pH 7.4 (final concentration 10 mM), and NaCl (final concentration 0.1 M) was added. The mixture was stirred for 18 hours, centrifuged, and redispersed in PBS 1×.

Figure 12:
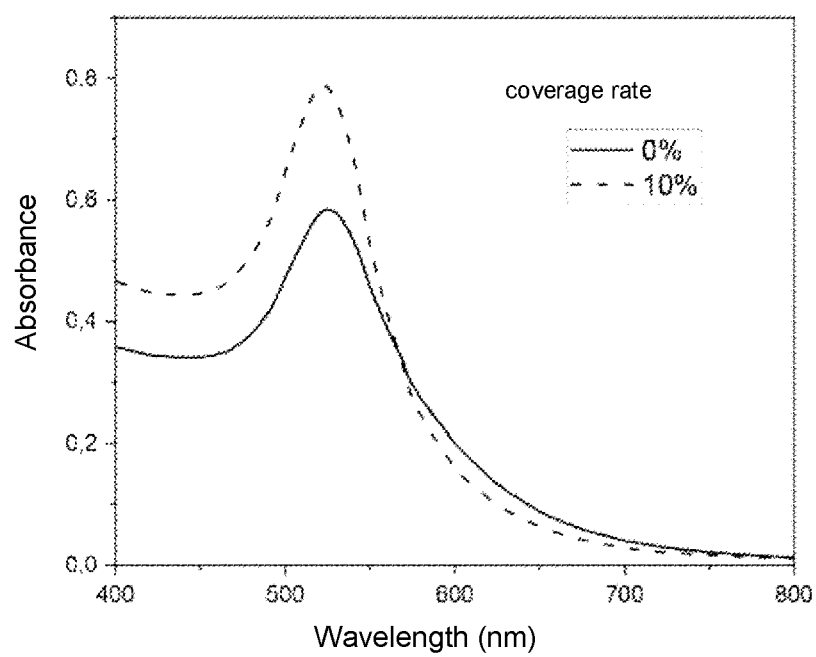
FIG. 12: Absorbance spectrum of NS pre-functionalized with molecules M (W=10%) and functionalized with DNA (z=25%) dispersed in PBS having different L-PEG coverage rates (X=0 or 10%), F=$CH_3$; NS size=20 nm. Commercial (ref 741965 Sigma Aldrich).
Figure 13:
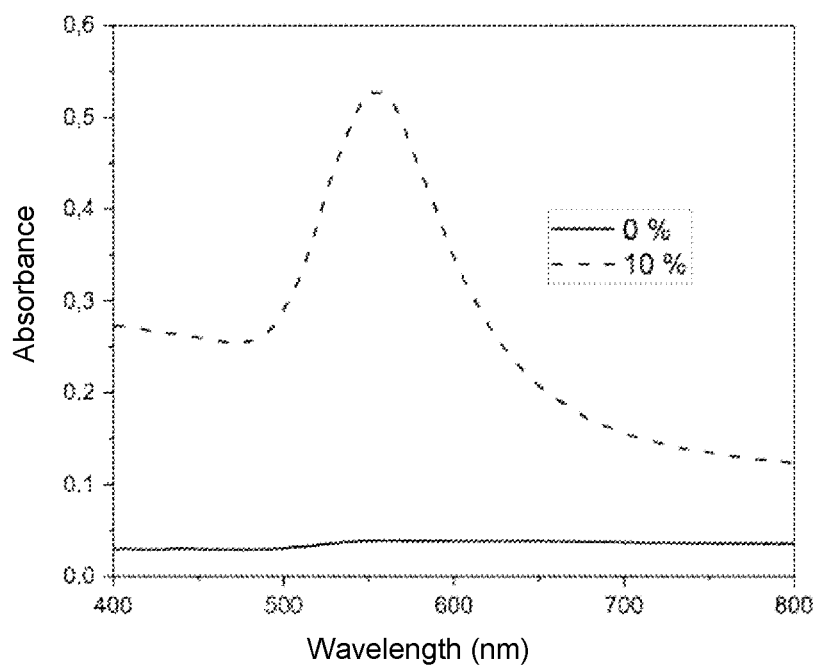
FIG. 13: Absorbance spectrum of NS pre-functionalized with molecules M (W=10%) and functionalized with DNA (Z=25%) dispersed in PBS having different L-PEG coverage rates (Y=0 or 10%), F=$CH_3$; NS size=80 nm commercial (ref 742023 Sigma Aldrich).

The data relating to the stability of the nanoparticles are set out in FIG. 12 for NPs of 20 nm, and in FIG. 13 for NPs of 80 nm.

An improvement in the stability of the NPs is noted when L-PEG molecules are added. Notably, the presence of a layer of L-PEG makes it possible to stabilize the NPs of 80 nm in PBS solution with a low level of molecules M (W=10%).

Example 9

Effect of Incubation Time of the NPs in the Solution Containing the Molecule M on the Stability A solution of molecules M is added to a solution of nanoparticles. The mixture is stirred for several minutes or hours (from 5 minutes to 24 hours), then 0.005% surfactant, a phosphate buffer solution of pH 7.4, and NaCl are added. The NPs are then dispersed in PBS (phosphate 10 nM, pH=7.4, and 0.1 M NaCl) in the presence of 0.005% surfactant.

Figure 14:
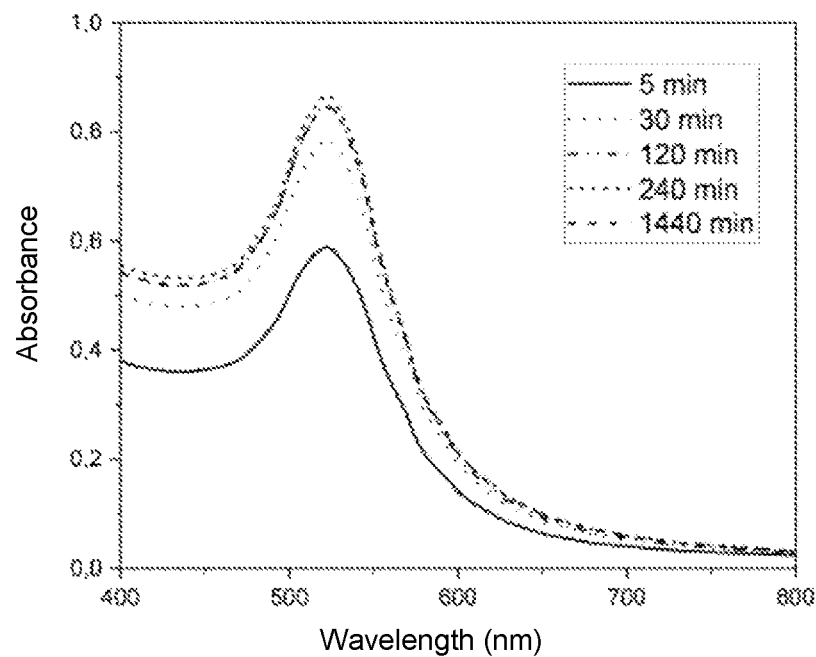
FIG. 14: Absorbance spectrum of NS pre-functionalized with molecules M in PBS+0.005% surfactant depending on the incubation time; NS of 20 nm; stirring time=5, 30, 120, 240 and 1440 minutes, M (n=11, m=4), W=40%.

The data relating to the stability of the nanoparticles are set out in FIG. 14.

It is noted that the coverage rate increases as a function of time, and reaches a maximum between 120 and 240 minutes of incubation. Continuing the incubation beyond this time period has no further effect on W.

Example 10

Reproducibility of the Method for Stabilizing the Nanoparticles

In order to confirm the reproducibility of the protocols, these were repeated three times on different days. The stability of the samples was characterized by UV-visible spectroscopy. Regarding the grafting of the thiolated DNA, the first supernatant, during the step of washing to remove the excess DNA, was analyzed by UV-visible spectroscopy.

Figure 15:
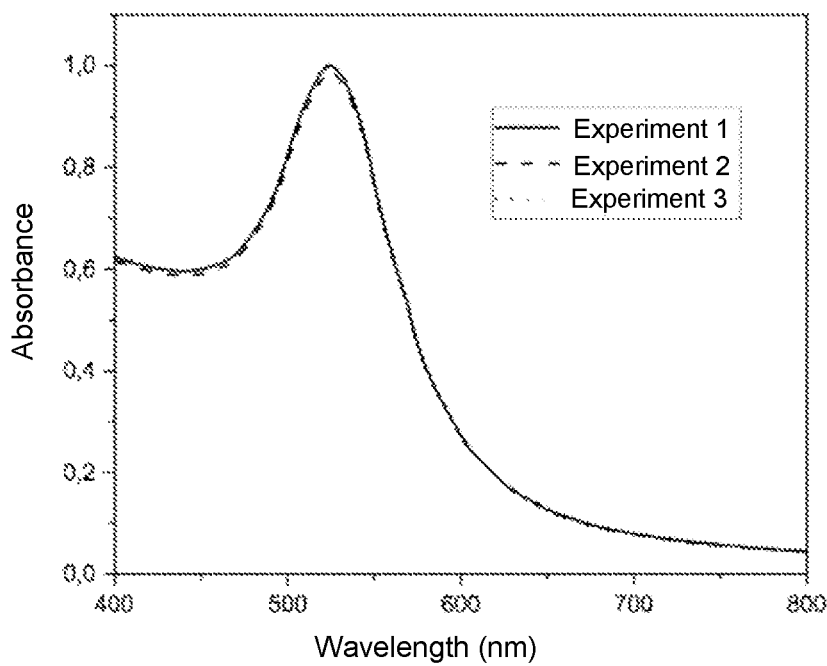
FIG. 15: Absorbance spectrum of NS pre-functionalized with molecules M and functionalized DNA (W=4% and Z=50%) corresponding to 3 different experiments. M (n=11, m=4), NP 20 nm.
Figure 16:
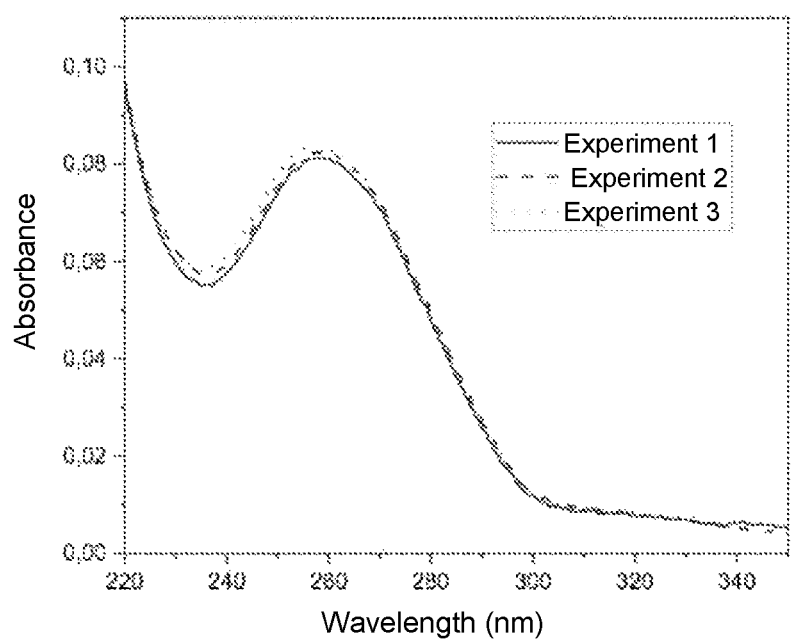
FIG. 16: Absorbance spectrum of supernatant of first washing of NS pre-functionalized with molecules M and functionalized DNA (W=4% and Z=50%) corresponding to 3 independent experiments. M (n=11, m=4), NS 20 nm.

The results are set out in FIG. 15 regarding the stability of solutions of functionalized NP, and in FIG. 16 regarding the supernatant obtained during the first step of washing of non-absorbed DNA.

It is noted that the UV-visible spectra comprise fine plasmon bands, which can be superimposed, suggesting that the nanoparticles NP pre-functionalized using molecules M and functionalized using DNA are stable, just as the identical absorbance intensity of the supernatants suggest that the same number of DNA has been attached to the NPs. In conclusion, these results confirm the reproducibility in the preparation of samples.

Example 11

The NPs Pre-Functionalized Using Molecules M are Stable for Several Months, in Water NPs of 20 nm were pre-functionalized using molecules M as described above, and then stored at 4° and in the dark for several months. The stability was studied by means of UV-visible spectroscopy. Typically, 1 ml of solution was withdrawn, and analyzed by means of a UVIKON spectrometer. The spectra obtained at different times were compared.

Figure 17:
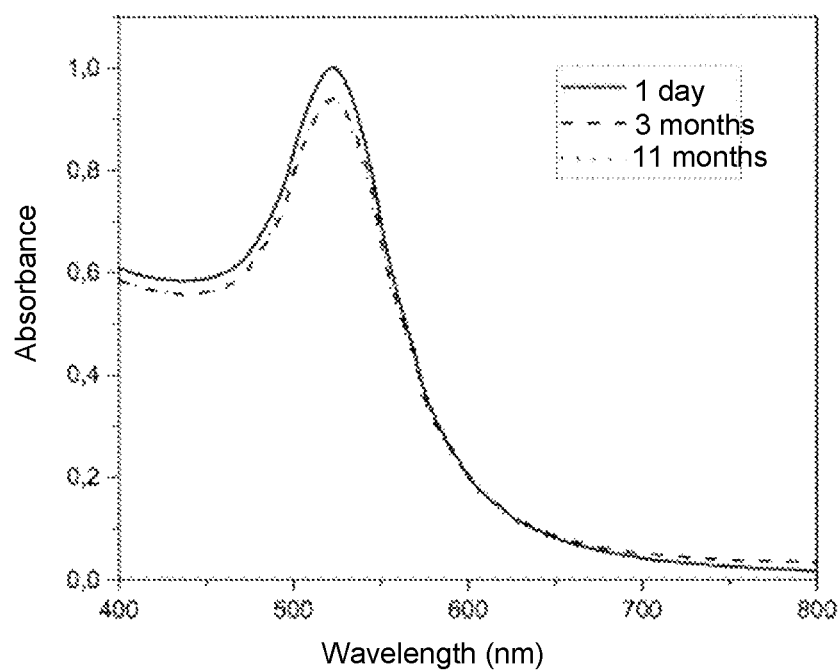
FIG. 17: Absorbance spectra of NS pre-functionalized with molecules M after one day, 3 and 11 months of preparation and storage at 4° C. NS 20 nm, M (n=11, m=4), where W=32%.

The data relating to the stability of the nanoparticles are set out in FIG. 17.

A good correlation of the absorbance spectra of NPs that are pre-functionalized using molecules M is observed following 1 day and 11 months of storage. The three spectra show fine plasmon bands without any displacement of the plasmon band, confirming that, after 11 months of storage at 4° C., the pre-functionalized NPs are still stable in water.

Example 12

The NPs Pre-Functionalized Using Molecules M and Functionalized Using a DNA are Stable for Several Months, in a PBS Solution NPs of 20 nm were pre-functionalized using molecules M and functionalized using DNA as described above, and then stored at 4° and in the dark for several months. The stability is evaluated by means of UV-visible spectroscopy. Typically, 1 ml of solution is withdrawn, and analyzed by means of a UVIKON spectrometer. The spectra obtained at different storage times are compared.

Figure 18:
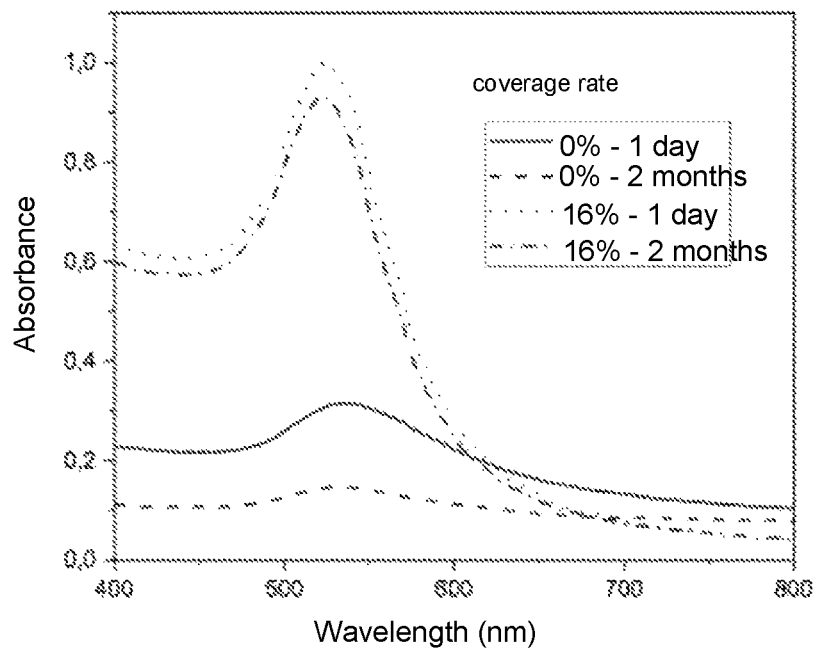
FIG. 18: Absorbance spectrum of NS pre-functionalized with molecules M and functionalized with thiolated DNA after 1 day and 2 months of storage at 4° C. M (n=11, m=4), where W=0 and 16%, and Z=12.5%.
Figure 19:
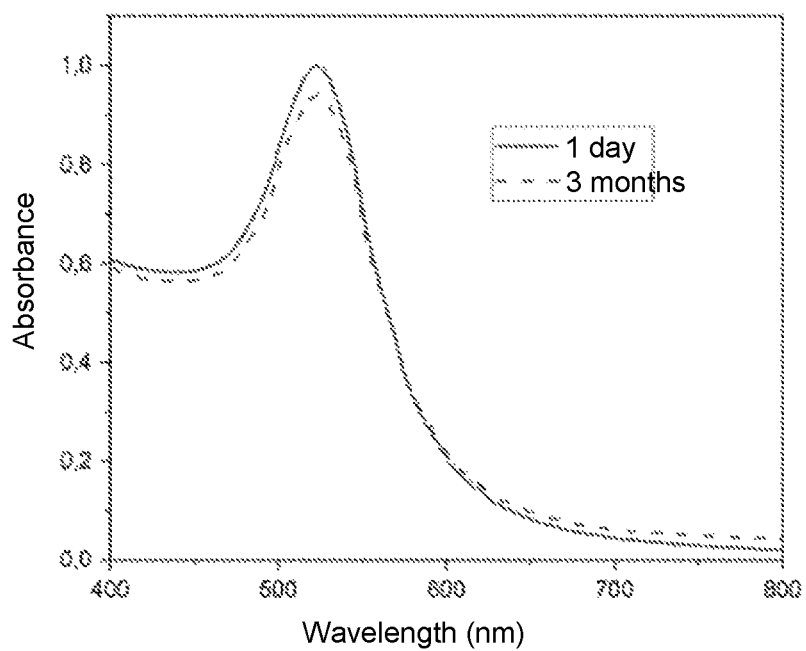
FIG. 19: Absorbance spectrum of NP pre-functionalized with molecules M and functionalized with thiolated DNA (W=32% and Z=25%) after 1 day and 3 months of storage at 4° C. NS size=20 nm, M (n=11, m=4).

The data relating to the stability of the nanoparticles are set out in FIGS. 18 and 19.

It is firstly noted that the presence of molecules M makes it possible to stabilize the NPs after preparation thereof and during storage thereof. These results show a good correlation of the spectra of NPs that are pre-functionalized and functionalized using a DNA, comparing those obtained following 1 day and 2-3 months of storage. The 2 spectra show two fine plasmon bands without any displacement of the plasmon band, confirming that, after 2-3 months of storage at 4° C., the NPs are still stable in PBS.

Example 13

The NPs that are Pre-Functionalized and Functionalized Using a DNA are Stable in Complex Media 10 µl of cellular extract were added to 1 ml of solution of NPs pre-functionalized using molecules M and functionalized using a thiolated DNA at 1 nM (the dilution of the complex medium is ×100). The mixture was stirred for 1 hour, then centrifuged, and redispersed in PBS 1×. The stability of the NPs and the absorbance intensity of the cellular medium in the supernatants are characterized by UV-visible spectroscopy. According to the Beer-Lambert law, the absorbance intensity is related to the concentration in solution. If the absorbance intensity of the cellular extract is similar to the absorbance intensity of the supernatants, this indicates that the biomolecule present in the cellular extract are not absorbed in a non-specific manner at the NPs.

Figure 20:
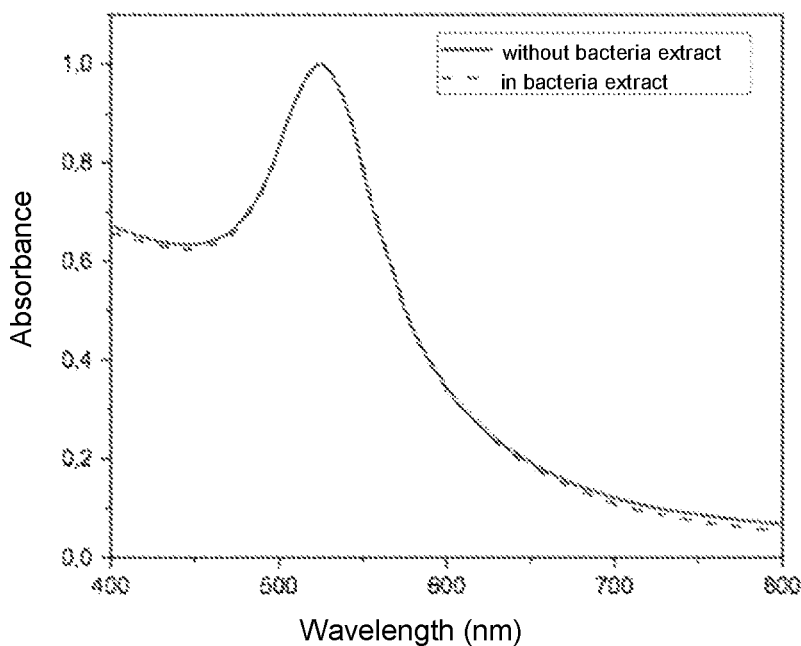
FIG. 20: UV-visible spectrum of NP pre-functionalized with molecules M and functionalized with thiolated DNA (W=30%, Z=12.5%) prior to addition of the cellular extract (solid line) after 1 hour of incubation in a cellular extract diluted 100× (dotted line). NS size=20 nm, M (n=11, m=4).
Figure 21:
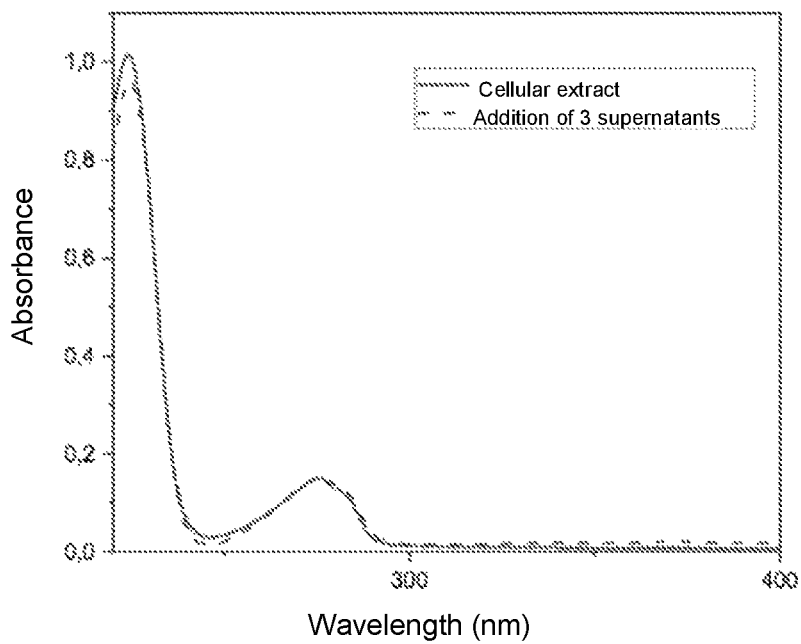
FIG. 21: Absorbance spectrum of the cellular extract diluted 100×, and the sum of the 3 supernatants, after centrifugation (dotted). NS size=20 nm, M (n=11, m=4) (W=30%, Z=12.5%).

The data relating to the stability of the nanoparticles are set out in FIGS. 20 and 21.

The absorbance spectra of the sample prior to addition of the cellular extract and following 1 hour of incubation were compared. It is noted that no aggregation takes place in the complex medium, suggesting that the particles are well protected. In order to determine whether there is non-specific adsorption, the particles were washed by means of centrifugation, in order to remove the cellular extract. The sum of the 3 supernatants after incubations of one hour was superimposed on the spectrum of the initial cellular extract. It was possible to observe that the spectra are superimposed, which suggests that there is little or no specific adsorption of proteins originating from the cellular extract at the surface of the functionalized NPs.

Example 14

The Pre-Functionalization of NPs with Molecules M Improves the Hybridization in Complex Media 1 µl complementary fluorescent DNA (Cy5) at 100 nM was added to a solution of 200 µl NP at 1.5 nM, functionalized using a DNA with or without pre-functionalization using molecules M. The total complementary DNA concentration was thus 500 pM. The hybridization took place over 2 hours of incubation at 37° C. in three different media: PBS 1×, cellular extract and human serum. The complex media are diluted 100 times. In order to distinguish the fluorescent DNAs, NPs functionalized with DNA, and NPs pre-functionalized prior to functionalization with the DNA, the samples were deposited in an agarose gel for electrophoresis. The electrophoresis makes it possible to separate and distinguish the hybridized nanoparticles and the complementary DNAs that are free in solution.

The hybridization of a complementary fluorescent strand with two types of nanoparticles, either NPs functionalized using DNA molecules only, or NPs pre-functionalized using a monolayer of molecules M and then functionalized using DNA molecules, was studied in three different media: PBS, cellular extract diluted 100×, and human serum diluted 100×. The nanoparticles used had been synthesized 2 months prior to being used, and stored at 4° C.

Figure 22:
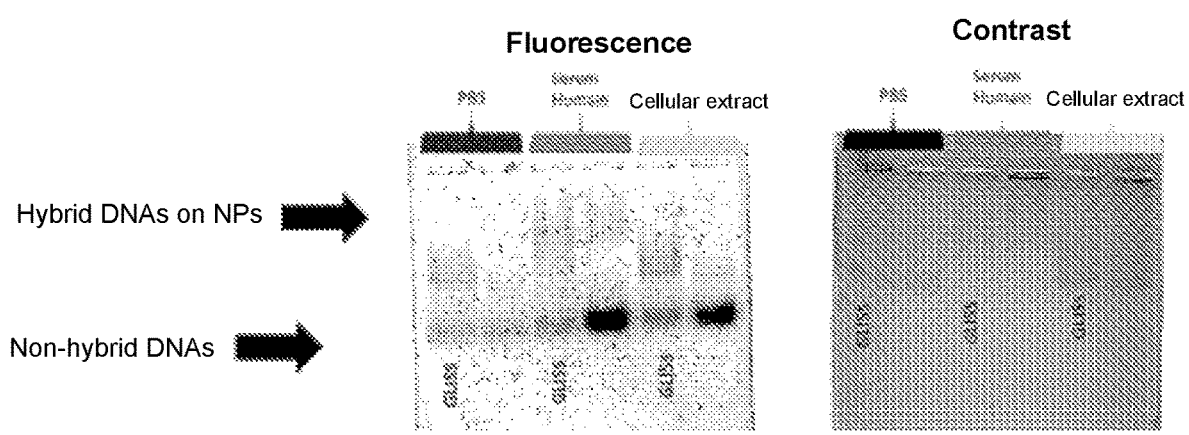
FIG. 22: Left-hand image: image of fluorescence of Cy5 in order to locate the complementary fluorescent DNA; right-hand image: contrast image of the gel in order to locate the nanoparticles. NS size=20 nm, M (n=11, m=4) (W=0 and 16%, Z=12.5%).

The results of this experiment are set out in FIG. 22.

It is observed that only the nanoparticles are visible, since the fluorophore alone is not excited. The migration distance of the nanoparticles NP functionalized using DNA, and that of the NPs pre-functionalized prior to functionalization using DNA, does not appear to be affected in the PBS and the cellular extract. In contrast, in human serum the migration distance varies vey slightly for the NPs that are pre-functionalized prior to functionalization, but varies more significantly for NPs functionalized using DNA (without molecules M), suggesting the possibility of non-specific absorption on these nanoparticles (visible by a slowing of the migration due to an increase in the size of the NPs). In the left-hand part of the figure, only the emission of the fluorescence is observed (black bands in the gel), indicating the position of the complementary DNA in the gel. Comparing the intensity of the bands and the position of the bands in FIG. 22, it is possible to correlate the position of the DNAs with the position of the NPs in the gel, and consequently the effectiveness of the hybridization. While in the PBS the effectiveness of the hybridization between the pre-functionalized nanoparticles and those which were not pre-functionalized does not appear to be affected, a clear difference is observed in complex media. Indeed, it appears that, for the samples without molecules M (i.e., DNA alone), the hybridization is affected, since the fluorescence corresponding to the free DNA is significantly more intense (less complementary DNA has hybridized to the DNA attached to the NPs). These results suggest that the hybridization effectiveness for the pre-functionalized sample is greater in complex media. It is possible to assume that, in a complex medium, the non-specific absorption of proteins on the NPs functionalized using DNA (but not pre-functionalized) prevents the hybridization between complementary DNA and DNA attached to the NPs.

Example 15

Evaluation of the Detection of Target Complementary DNA in Different Media

The detection of a single strand of target DNA (cDNA) was permitted, following the hybridization effectiveness between the complementary target fluorescent DNA (Cy5) and the DNA immobilized on the nanoparticles pre-functionalized using the molecule M. Once the DNAs had hybridized, two gel electrophoreses were carried out before centrifugation and after centrifugation of the NPs. The centrifugation makes it possible to concentrate the NPs in order to achieve an improved visualization of the complementary fluorescent DNA at the surface of the NPs.

Hybridization protocol followed: 50 pM at 1 nM of fluorescent complementary DNA were added to a suspension of NPs at 2 nM (size of NPs=20 nm, M (n=11 and m=4), W=16% and Z=12.5%). The mixture is incubated for 2 hours at 37° C., either in the PBS, or in commercial human serum (dilution 100) (Thermofisher, Normal Human Serum, ref. 31876).

A gel migration of the NPs was carried out (data not shown). The "image of nanoparticles" part shows the location of the bioconjugated NPs, and the "image of fluorescence" part shows the location of the fluorescent complementary DNA. The control corresponds to a free fluorescent complementary DNA. Different concentrations were charged from 50 pM to 1 nM.

These results confirm that the hybridization has occurred because the fluorescence is correlated to the position of the nanoparticles. The fluorescence is observed for the range of concentration of target DNA of up to 50 pM, in PBS or in human serum. The presence of complex media does not prevent the hybridization, even at a low concentration of target DNA.

CONCLUSION

The hybridization on NPs of DNA probes makes it possible to detect the complementary DNA of 50 pM at 1 nM in PBS or human serum.

The invention claimed is:

1. A nanoparticle comprising a metal surface pre-functionalized with a self-assembled protective monolayer formed by a matrix of molecules M of formula (1): $HS(CH_2)n \ (OCH_2CH_2)m \ OH$, in which:
   n represents the number of $CH_2$, where $3 \leq n \leq 11$; and
   m represents the number of ethylene glycol, where $1 \leq m \leq 12$;
   the molecules bearing a thiol function at one end thereof, the other end thereof being inert;
   wherein a coverage rate of the monolayer is between 1.5% and 99%, and the nanoparticle is further functionalized with at least one L-PEG molecule of formula (7): $SH-CH_2CH_2(CH_2CH_2O)_qO-F$, in which:
   q represents the number of ethylene glycol, where $20 \leq q \leq 500$; and
   F represents a functional group selected from among $CH_3$, OH, COOH or $NH_2$, a coverage rate of the L-PEG molecule being at least 1%.

2. The nanoparticle of claim 1, wherein the nanoparticle is further functionalized with at least one thiolated molecule, the thiolated molecule being either:
   a PEG-F linker molecule of formula (8): $HS(CH_2)_r (OCH_2CH_2)_p \ O-F$, in which:
   r represents the number of $CH_2$ and is a whole number greater than or equal to 3;
   p represents the number of ethylene glycol, where $2 \leq p \leq 12$; and
   F represents a functional group selected from among $CH_3$, COOH or $NH_2$, the linker molecule bearing a thiol function at one end thereof and bearing an active or reactive group that is capable of interacting with a biomolecule at the other end thereof; or
   a biomolecule comprising a thiol function.

3. The nanoparticle of claim 2, wherein the thiolated molecule is a the PEG-F linker molecule, and wherein F is COOH, and a coverage rate of which is at least 1%.

4. The nanoparticle of claim 2, wherein the nanoparticle is further functionalized with at least one biomolecule bound to the linker molecule.

5. The nanoparticle of claim 2, wherein the thiolated biomolecule is a thiolated DNA, a coverage rate of which is at least 10%.

* * * * *